(12) United States Patent
Alexander

(10) Patent No.: US 8,937,033 B2
(45) Date of Patent: *Jan. 20, 2015

(54) USE OF PHOSPHATED ALCANOLS AS DISPERSANTS, EMULSIFIERS, HYDROTROPES, WETTING AGENTS AND COMPATABILITY AGENTS IN AGRICULTURAL COMPOSITIONS

(75) Inventor: Mark Alexander, Fort Worth, TX (US)

(73) Assignee: Akzo Nobel N.V., Arnhem (NL)

( * ) Notice: Subject to any disclaimer, the term of this patent is extended or adjusted under 35 U.S.C. 154(b) by 596 days.

This patent is subject to a terminal disclaimer.

(21) Appl. No.: 11/632,381

(22) PCT Filed: Jul. 13, 2005

(86) PCT No.: PCT/US2005/024777
§ 371 (c)(1), (2), (4) Date: Jan. 12, 2007

(87) PCT Pub. No.: WO2006/019772
PCT Pub. Date: Feb. 23, 2006

(65) Prior Publication Data
US 2008/0051289 A1 Feb. 28, 2008

Related U.S. Application Data

(60) Provisional application No. 60/608,167, filed on Sep. 8, 2004.

(30) Foreign Application Priority Data

Jul. 15, 2004 (EP) .................................. 04077043

(51) Int. Cl.
*A01N 25/22* (2006.01)
*A01P 13/00* (2006.01)
*A01N 25/30* (2006.01)

(52) U.S. Cl.
CPC ................................ *A01N 25/30* (2013.01)
USPC .......................................... 504/358; 514/772

(58) Field of Classification Search
CPC ...................................................... A01N 25/30
USPC ............................................ 504/358; 514/772
See application file for complete search history.

(56) References Cited

U.S. PATENT DOCUMENTS

| | | | | |
|---|---|---|---|---|
| 2,871,155 A * | 1/1959 | Vellaire et. al. | | 514/328 |
| 3,869,412 A * | 3/1975 | Waag | | 510/467 |
| 4,975,110 A | 12/1990 | Puritch et al. | | 71/113 |
| 4,986,851 A | 1/1991 | Dietz et al. | | 106/503 |
| 5,679,351 A * | 10/1997 | Walter et al. | | 424/725 |
| 6,432,884 B1 | 8/2002 | Lachut | | 504/363 |

FOREIGN PATENT DOCUMENTS

| | | | | |
|---|---|---|---|---|
| CH | 481 953 A | 11/1969 | | C08F 1/13 |
| EP | 0 256 427 A2 | 2/1988 | | C09B 67/20 |
| GB | 1142425 | 2/1969 | | C08F 1/14 |
| GB | 2 049 427 A | 12/1980 | | A01N 25/22 |
| WO | WO 2006/005721 A1 | 1/2006 | | |

OTHER PUBLICATIONS

International Search Report for International Application No. PCT/US2005/024777, Jul. 13, 2005.
Linfield et al. "Anionic Surfactants," Surfactant Science Series, vol. 7, Part II, pp. 504-511 (1976).

* cited by examiner

*Primary Examiner* — Janet Epps-Smith
*Assistant Examiner* — Courtney Brown
(74) *Attorney, Agent, or Firm* — Matthew D. Kellam

(57) ABSTRACT

The present invention relates to the use of phosphated 2-propylheptanol, phosphated 2-proyplheptanol alkoxylate and/or mixtures thereof in agricultural formulations. The invention also relates to agricultural formulations comprising the aforementioned adjuvants, and to methods of treating a plant with the agricultural formulations of the invention.

16 Claims, 1 Drawing Sheet

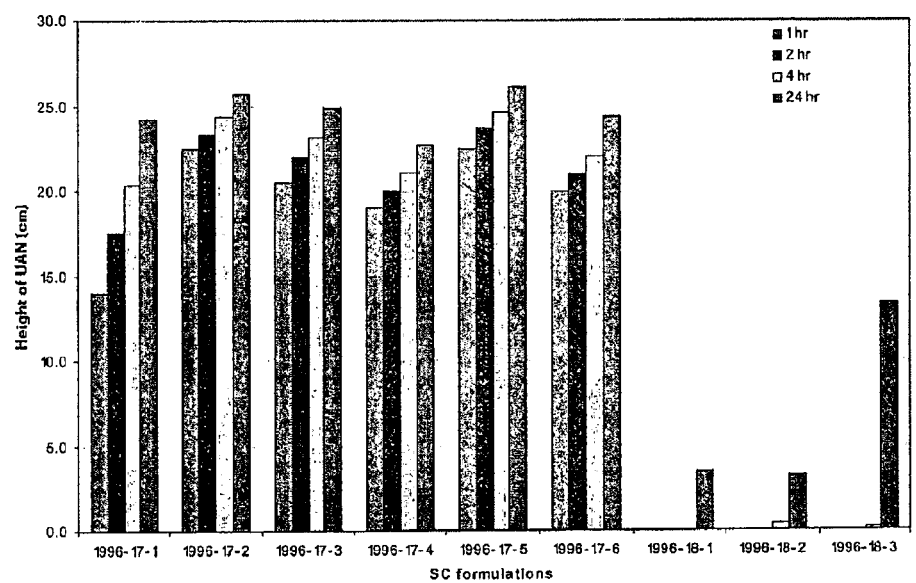

USE OF PHOSPHATED ALCANOLS AS DISPERSANTS, EMULSIFIERS, HYDROTROPES, WETTING AGENTS AND COMPATABILITY AGENTS IN AGRICULTURAL COMPOSITIONS

The present invention relates to the use of phosphated 2-propylheptanol or a phosphated 2-propylheptanol alkoxylate as an adjuvant in agricultural formulations. More specifically, it relates to the use of phosphated hydroxyl compounds as a dispersant, emulsifier, hydrotrope, wetting agent, compatibility agent and the like in agricultural formulations.

BACKGROUND OF THE INVENTION

The agricultural chemical formulator has the difficult task of creating a product that balances bioefficacy, toxicity, cost, shelf life and user friendliness. Of particular importance to the activity of an agricultural formulation is the ability of an aqueous solution to spread evenly over a surface, the so-called wetting ability, and the effective uptake of the active ingredient by the plant to be treated. For example, in agricultural formulations, efficacy benefits from a good wetting of the plant surface and uptake of the active ingredient.

Adjuvants are added to agricultural formulations to improve activity, thereby reducing the amounts of active ingredients necessary, resulting in lower application cost. They generally take the form of surface-active or salt-like compounds and depending on their mode of action, they are classified as modifiers, activators, fertilizers and/or pH buffers.

Surfactants are generally regarded as modifiers and/or activators as they improve wetting properties and uptake of the active ingredients in the agricultural formulation. Additionally, some surfactants improve the solubility of active ingredients in formulations thereby eliminating serious issues such as product separation and/or crystallization.

Anionic, cationic, amphoteric and nonionic surfactants are all known and used in agricultural applications depending on the desired effect. For example, nonionic surfactants are known to be good wetting agents, and are often present in agricultural formulations. Many nonionic surfactants are not soluble enough in solutions with a high amount of electrolytes, such as alkali and/or alkaline complexing agents, salts, and the like and therefore need the presence of a hydrotrope to improve the solubility. A number of hydrotropes for nonionic surfactants have been described in various publications. Examples of such hydrotropes are ethanol, sodium xylene sulphonate, sodium cumene sulphonate, alkyl glycosides, and phosphated alkoxylated alcohols.

However, there is still a need for new efficient surfactants that can improve activity, act as effective hydrotropes, and are compatible for the achievement of stable formulations delivering optimal performance. The objective of the present invention is, therefore, to find a new hydrotrope that is efficient in formulating agricultural compositions, which compositions will remain homogeneous upon dilution, and where the performance of the compositions is good.

Accordingly, it is an object of the present invention to provide an improved agricultural adjuvant. It is also an object of the invention to provide a stable, agricultural formulation having improved activity. These and other objects are achieved by the adjuvants/formulations of the present invention.

SUMMARY OF THE INVENTION

The present invention relates to the use of phosphated 2-propylheptanol, phosphated 2-propylheptanol alkoxylate and/or mixtures thereof as agricultural adjuvants. The invention also relates to agricultural formulations comprising same, and to methods of treating a plant with the agricultural formulations of the invention.

DETAILED DESCRIPTION OF THE DRAWINGS

FIG. 1 shows the Atrazine formulation performance of several samples described in Table 8.

DETAILED DESCRIPTION OF THE INVENTION

The invention relates to the use of phosphated 2-propylheptanol or phosphated 2-propylheptanol alkoxylates as a hydrotrope in agricultural formulations. More specifically, it relates to an agricultural adjuvant that comprises at least one phosphated hydroxyl compound. The adjuvant of the invention can effectively be utilized as a dispersant, emulsifier, hydrotrope, wetting agent, compatibility agent and/or the like in agricultural formulations. In this regard, the inventors have found that phosphated 2-propylheptanol or a phosphated 2-propylheptanol alkoxylate where the alkoxylate on the average comprises 1-20, preferably 1-15, more preferably 2-10, and most preferably 2-6 ethyleneoxy units and 0-3, preferably 0-2 propyleneoxy and/or butyleneoxy units, is an efficient hydrotrope and activity improver in agricultural formulations. The adjuvants of the invention improve wetting and uptake of active ingredients by a plant, resulting in a higher activity at a given application rate.

In another embodiment, the invention relates to aqueous agricultural formulations comprising at least one agricultural active, and 0.1-30, preferably 0.1-20, and most preferably 0.1-10% by weight of the adjuvant of the present invention.

The adjuvants of the invention can be used with any active ingredient in order to improve efficacy by improving the dispersion or emulsions properties in the application tank, or modifying the spreading and/or penetration properties of the spray solution on the plant. Examples of active ingredients include, but are not limited to herbicides, fungicides, insecticides, plant growth regulators and the like.

The following is a non-limiting list of active ingredients that can be employed:

Herbicides (Examples, but not Limited to):
    amide herbicides
    allidochlor
    beflubutamid
    benzadox
    benzipram
    bromobutide
    cafenstrole
    CDEA
    cyprazole
    dimethenamid
        dimethenamid-P
    diphenamid
    epronaz
    etnipromid
    fentrazamide
    flupoxam
    fomesafen
    halosafen
    isocarbamid
    isoxaben
    napropamide
    naptalam
    pethoxamid
    propyzamide quinonamid
tebutam
  anilide herbicides
    chloranocryl
    cisanilide
    clomeprop
    cypromid
    diflufenican
    etobenzanid
    fenasulam
    flufenacet
    flufenican
    mefenacet
    mefluidide
    metamifop
    monalide
    naproanilide
    pentanochlor
    picolinafen
    propanil
    arylalanine herbicides
      benzoylprop
      flamprop
        flamprop-M
    chloroacetanilide herbicides
      acetochlor
      alachlor
      butachlor
      butenachlor
      delachlor
      diethatyl
      dimethachlor
      metazachlor
      metolachlor
        S-metolachlor
      pretilachlor
      propachlor
      propisochlor
      prynachlor
      terbuchlor
      thenylchlor
      xylachlor
  sulfonanilide herbicides
    benzofluor
    cloransulam
    diclosulam
    florasulam
    flumetsulam
    metosulam
    perfluidone
    pyrimisulfan
    profluazol
sulfonamide herbicides
  asulam
  carbasulam
  fenasulam
  oryzalin
  penoxsulam
    thioamide herbicides
      bencarbazone
      chlorthiamid
antibiotic herbicides
  bilanafos
aromatic acid herbicides
  benzoic acid herbicides
    chloramben
    dicamba
    2,3,6-TBA
    tricamba
      pyrimidinyloxybenzoic acid herbicides
        bispyribac
        pyriminobac
      pyrimidinylthiobenzoic acid herbicides
        pyrithiobac
  phthalic acid herbicides
    chlorthal
  picolinic acid herbicides
    aminopyralid
    clopyralid
    picloram
  quinolinecarboxylic acid herbicides
    quinclorac
    quinmerac
arsenical herbicides
  cacodylic acid
  CMA
  DSMA
  hexaflurate
  MAA
  MAMA
  MSMA
  potassium arsenite
  sodium arsenite
benzoylcyclohexanedione herbicides
  mesotrione
  sulcotrione
benzofuranyl alkylsulfonate herbicides
  benfuresate
  ethofumesate
carbamate herbicides
  asulam
  carboxazole
  chlorprocarb
  dichlormate
  fenasulam
  karbutilate
  terbucarb
  carbanilate herbicides
    barban
    BCPC
    carbasulam
    carbetamide
    CEPC
    chlorbufam
    chlorpropham
    CPPC
    desmedipham
    phenisopham
    phenmedipham
    phenmedipham-ethyl
    propham
    swep
cyclohexene oxime herbicides
  alloxydim
  butroxydim
  clethodim
  cloproxydim
  cycloxydim
  profoxydim
  sethoxydim
  tepraloxydim
  tralkoxydim
cyclopropylisoxazole herbicides
  isoxachlortole isoxaflutole
dicarboximide herbicides
benzfendizone
cinidon-ethyl
flumezin
flumiclorac
flumioxazin
flumipropyn
dinitroaniline herbicides
benfluralin
butralin
dinitramine
ethalfluralin
fluchloralin
isopropalin
methalpropalin
nitralin
oryzalin
pendimethalin
prodiamine
profluralin
trifluralin
dinitrophenol herbicides
dinofenate
dinoprop
dinosam
dinoseb
dinoterb
DNOC
etinofen
medinoterb
diphenyl ether herbicides
ethoxyfen
   nitrophenyl ether herbicides
      aclonifen
      acifluorfen
      bifenox
      chlomethoxyfen
      chlornitrofen
      etnipromid
      fluorodifen
      fluoroglycofen
      fluoronitrofen
      fomesafen
      furyloxyfen
      halosafen
      lactofen
      nitrofen
      nitrofluorfen
      oxyfluorfen
dithiocarbamate herbicides
dazomet
metam
halogenated aliphatic herbicides
alorac
chloropon
dalapon
flupropanate
hexachloroacetone
iodomethane
methyl bromide
monochloroacetic acid
SMA
TCA
imidazolinone herbicides
imazamethabenz
imazamox
imazapic
imazapyr
imazaquin
imazethapyr
inorganic herbicides
ammonium sulfamate
borax
calcium chlorate
copper sulfate
ferrous sulfate
potassium azide
potassium cyanate
sodium azide
sodium chlorate
sulfuric acid
nitrile herbicides
bromobonil
bromoxynil
chloroxynil
dichlobenil
iodobonil
ioxynil
pyraclonil
organophosphorus herbicides
amiprofos-methyl
anilofos
bensulide
bilanafos
butamifos
2,4-DEP
DMPA
EBEP
fosamine
glufosinate
glyphosate
piperophos
phenoxy herbicides
bromofenoxim
clomeprop
2,4-DEB
2,4-DEP
difenopenten
disul
erbon
etnipromid
fenteracol
trifopsime
   phenoxyacetic herbicides
      4-CPA
      2,4-D
      3,4-DA
      MCPA
      MCPA-thioethyl
      2,4,5-T
   phenoxybutyric herbicides
      4-CPB
      2,4-DB
      3,4-DB
      MCPB
      2,4,5-TB
   phenoxypropionic herbicides
      cloprop
      4-CPP
      dichlorprop
         dichlorprop-P
      3,4-DP
      fenoprop mecoprop
  mecoprop-P
  aryloxyphenoxypropionic herbicides
    chlorazifop
    clodinafop
    clofop
    cyhalofop
    diclofop
    fenoxaprop
      fenoxaprop-P
    fenthiaprop
    fluazifop
      fluazifop-P
    haloxyfop
      haloxyfop-P
    isoxapyrifop
    metamifop
    propaquizafop
    quizalofop
      quizalofop-P
    trifop
phenylenediamine herbicides
  dinitramine
  prodiamine
phenyl pyrazolyl ketone herbicides
  benzofenap
  pyrasulfotole
  pyrazolynate
  pyrazoxyfen
  topramezone
pyrazolylphenyl herbicides
  fluazolate
  pyraflufen
pyridazine herbicides
  credazine
  pyridafol
  pyridate
pyridazinone herbicides
  brompyrazon
  chloridazon
  dimidazon
  flufenpyr
  metflurazon
  norflurazon
  oxapyrazon
  pydanon
pyridine herbicides
  aminopyralid
  cliodinate
  clopyralid
  dithiopyr
  fluroxypyr
  haloxydine
  picloram
  picolinafen
  pyriclor
  thiazopyr
  triclopyr
pyrimidinediamine herbicides
  iprymidam
  tioclorim
quaternary ammonium herbicides
  cyperquat
  diethamquat
  difenzoquat
  diquat
  morfamquat
  paraquat
thiocarbamate herbicides
  butylate
  cycloate
  di-allate
  EPTC
  esprocarb
  ethiolate
  isopolinate
  methiobencarb
  molinate
  orbencarb
  pebulate
  prosulfocarb
  pyributicarb
  sulfallate
  thiobencarb
  tiocarbazil
  tri-allate
  vernolate
thiocarbonate herbicides
  dimexano
  EXD
  proxan
thiourea herbicides
  methiuron
triazine herbicides
  dipropetryn
  triaziflam
  trihydroxytriazine
  chlorotriazine herbicides
    atrazine
    chlorazine
    cyanazine
    cyprazine
    eglinazine
    ipazine
    mesoprazine
    procyazine
    proglinazine
    propazine
    sebuthylazine
    simazine
    terbuthylazine
    trietazine
  methoxytriazine herbicides
    atraton
    methometon
    prometon
    secbumeton
    simeton
    terbumeton
  methylthiotriazine herbicides
    ametryn
    aziprotryne
    cyanatryn
    desmetryn
    dimethametryn
    methoprotryne
    prometryn
    simetryn
    terbutryn
triazinone herbicides
  ametridione
  amibuzin
  hexazinone
  isomethiozin metamitron
metribuzin
triazole herbicides
  amitrole
  cafenstrole
  epronaz
  flupoxam
triazolone herbicides
  amicarbazone
  bencarbazone
  carfentrazone
  flucarbazone
  propoxycarbazone
  sulfentrazone
triazolopyrimidine herbicides
  cloransulam
  diclosulam
  florasulam
  flumetsulam
  metosulam
  penoxsulam
uracil herbicides
  butafenacil
  bromacil
  flupropacil
  isocil
  lenacil
  terbacil
urea herbicides
  benzthiazuron
  cumyluron
  cycluron
  dichloralurea
  diflufenzopyr
  isonoruron
  isouron
  methabenzthiazuron
  monisouron
  noruron
  phenylurea herbicides
    anisuron
    buturon
    chlorbromuron
    chloreturon
    chlorotoluron
    chloroxuron
    daimuron
    difenoxuron
    dimefuron
    diuron
    fenuron
    fluometuron
    fluothiuron
    isoproturon
    linuron
    methiuron
    methyldymron
    metobenzuron
    metobromuron
    metoxuron
    monolinuron
    monuron
    neburon
    parafluron
    phenobenzuron
    siduron
    tetrafluron
    thidiazuron
  sulfonylurea herbicides
    pyrimidinylsulfonylurea herbicides
      amidosulfuron
      azimsulfuron
      bensulfuron
      chlorimuron
      cyclosulfamuron
      ethoxysulfuron
      flazasulfuron
      flucetosulfuron
      flupyrsulfuron
      foramsulfuron
      halosulfuron
      imazosulfuron
      mesosulfuron
      nicosulfuron
      orthosulfamuron
      oxasulfuron
      primisulfuron
      pyrazosulfuron
      rimsulfuron
      sulfometuron
      sulfosulfuron
      trifloxysulfuron
    triazinylsulfonylurea herbicides
      chlorsulfuron
      cinosulfuron
      ethametsulfuron
      iodosulfuron
      metsulfuron
      prosulfuron
      thifensulfuron
      triasulfuron
      tribenuron
      triflusulfuron
      tritosulfuron
    thiadiazolylurea herbicides
      buthiuron
      ethidimuron
      tebuthiuron
      thiazafluron
      thidiazuron
unclassified herbicides
  acrolein
  ally alcohol
  azafenidin
  benazolin
  bentazone
  benzobicyclon
  buthidazole
  calcium cyanamide
  cambendichlor
  chlorfenac
  chlorfenprop
  chlorflurazole
  chlorflurenol
  cinmethylin
  clomazone
  CPMF
  cresol
  ortho-dichlorobenzene
  dimepiperate
  endothal
  fluoromidine
  fluridone
  flurochloridone flurtamone
fluthiacet
indanofan
methazole
methyl isothiocyanate
nipyraclofen
OCH
oxadiargyl
oxadiazon
oxaziclomefone
pentachlorophenol
pentoxazone
phenylmercury acetate
pinoxaden
prosulfalin
pyribenzoxim
pyriftalid
quinoclamine
rhodethanil
sulglycapin
thidiazimin
tridiphane
trimeturon
tripropindan
tritac
Fungicides Include, but are not Limited to:
  aliphatic nitrogen fungicides
  butylamine
  cymoxanil
  dodicin
  dodine
  guazatine
  iminoctadine
  amide fungicides
  carpropamid
  chloraniformethan
  cyflufenamid
  diclocymet
  ethaboxam
  fenoxanil
  flumetover
  furametpyr
  mandipropamid
  penthiopyrad
  prochloraz
  quinazamid
  silthiofam
  triforine
    acylamino acid fungicides
    benalaxyl
    benalaxyl-M
    furalaxyl
    metalaxyl
    metalaxyl-M
    pefurazoate
    anilide fungicides
    benalaxyl
    benalaxyl-M
    boscalid
    carboxin
    fenhexamid
    metalaxyl
    metalaxyl-M
    metsulfovax
    ofurace
    oxadixyl
    oxycarboxin
    pyracarbolid
    thifluzamide
    tiadinil
      benzanilide fungicides
      benodanil
      flutolanil
      mebenil
      mepronil
      salicylanilide
      tecloftalam
      furanilide fungicides
      fenfuram
      furalaxyl
      furcarbanil
      methfuroxam
      sulfonanilide fungicides
      flusulfamide
    benzamide fungicides
    benzohydroxamic acid
    fluopicolide
    tioxymid
    trichlamide
    zarilamid
    zoxamide
    furamide fungicides
    cyclafuramid
    furmecyclox
    phenylsulfamide fungicides
    dichlofluanid
    tolylfluanid
    sulfonamide fungicides
    amisulbrom
    cyazofamid
    valinamide fungicides
    benthiavalicarb
    iprovalicarb
  antibiotic fungicides
  aureofungin
  blasticidin-S
  cycloheximide
  griseofulvin
  kasugamycin
  natamycin
  polyoxins
  polyoxorim
  streptomycin
  validamycin
    strobilurin fungicides
    azoxystrobin
    dimoxystrobin
    fluoxastrobin
    kresoxim-methyl
    metominostrobin
    orysastrobin
    picoxystrobin
    pyraclostrobin
    trifloxystrobin
  aromatic fungicides
  biphenyl
  chlorodinitronaphthalene
  chloroneb
  chlorothalonil
  cresol
  dicloran
  hexachlorobenzene
  pentachlorophenol
  quintozene sodium pentachlorophenoxide
tecnazene
benzimidazole fungicides
benomyl
carbendazim
chlorfenazole
cypendazole
debacarb
fuberidazole
mecarbinzid
rabenzazole
thiabendazole
benzimidazole precursor fungicides
furophanate
thiophanate
thiophanate-methyl
benzothiazole fungicides
bentaluron
chlobenthiazone
TCMTB
bridged diphenyl fungicides
bithionol
dichlorophen
diphenylamine
carbamate fungicides
benthiavalicarb
furophanate
iprovalicarb
propamocarb
thiophanate
thiophanate-methyl
   benzimidazolylcarbamate fungicides
   benomyl
   carbendazim
   cypendazole
   debacarb
   mecarbinzid
   carbanilate fungicides
   diethofencarb
conazole fungicides
   conazole fungicides (imidazoles)
   climbazole
   clotrimazole
   imazalil
   oxpoconazole
   prochloraz
   triflumizole
   see also imidazole fungicides
   conazole fungicides (triazoles)
   azaconazole
   bromuconazole
   cyproconazole
   diclobutrazol
   difenoconazole
   diniconazole
   diniconazole-M
   epoxiconazole
   etaconazole
   fenbuconazole
   fluquinconazole
   flusilazole
   flutriafol
   furconazole
   furconazole-cis
   hexaconazole
   imibenconazole
   ipconazole
   metconazole
   myclobutanil
   penconazole
   propiconazole
   prothioconazole
   quinconazole
   simeconazole
   tebuconazole
   tetraconazole
   triadimefon
   triadimenol
   triticonazole
   uniconazole
   uniconazole-P
   see also triazole fungicides
copper fungicides
   Bordeaux mixture
   Burgundy mixture
   Cheshunt mixture
   copper acetate
   copper carbonate, basic
   copper hydroxide
   copper naphthenate
   copper oleate
   copper oxychloride
   copper sulfate
   copper sulfate, basic
   copper zinc chromate
   cufraneb
   cuprobam
   cuprous oxide
   mancopper
   oxine copper
dicarboximide fungicides
   famoxadone
   fluoroimide
      dichlorophenyl dicarboximide fungicides
      chlozolinate
      dichlozoline
   iprodione
   isovaledione
   myclozolin
   procymidone
   vinclozolin
   phthalimide fungicides
   captafol
   captan
   ditalimfos
   folpet
      thiochlorfenphim
dinitrophenol fungicides
   binapacryl
   dinobuton
   dinocap
   dinocap-4
   dinocap-6
   dinocton
   dinopenton
   dinosulfon
   dinoterbon
   DNOC
dithiocarbamate fungicides
   azithiram
   carbamorph
   cufraneb
   cuprobam
   disulfiram ferbam
metam
nabam
tecoram
thiram
ziram
  cyclic dithiocarbamate fungicides
  dazomet
  etem
  milneb
  polymeric dithiocarbamate fungicides
  mancopper
  mancozeb
  maneb
  metiram
  polycarbamate
  propineb
  zineb
imidazole fungicides
cyazofamid
fenamidone
fenapanil
glyodin
iprodione
isovaledione
pefurazoate
triazoxide
see also conazole fungicides (imidazoles)
inorganic fungicides
potassium azide
potassium thiocyanate
sodium azide
sulfur
see also copper fungicides
see also inorganic mercury fungicides
mercury fungicides
  inorganic mercury fungicides
  mercuric chloride
  mercuric oxide
  mercurous chloride
  organomercury fungicides
  (3-ethoxypropyl)mercury bromide
  ethylmercury acetate
  ethylmercury bromide
  ethylmercury chloride
  ethylmercury 2,3-dihydroxypropyl mercaptide
  ethylmercury phosphate
  N-(ethylmercury)-p-toluenesulphonanilide
  hydrargaphen
  2-methoxyethylmercury chloride
  methylmercury benzoate
  methylmercury dicyandiamide
  methylmercury pentachlorophenoxide
  8-phenylmercurioxyquinoline
  phenylmercuriurea
  phenylmercury acetate
  phenylmercury chloride
  phenylmercury derivative of pyrocatechol
  phenylmercury nitrate
  phenylmercury salicylate
  thiomersal
  tolylmercury acetate
morpholine fungicides
aldimorph
benzamorf
carbamorph
dimethomorph
dodemorph
fenpropimorph
flumorph
tridemorph
organophosphorus fungicides
ampropylfos
ditalimfos
edifenphos
fosetyl
hexylthiofos
iprobenfos
phosdiphen
pyrazophos
tolclofos-methyl
triamiphos
organotin fungicides
decafentin
fentin
tributyltin oxide
oxathiin fungicides
carboxin
oxycarboxin
oxazole fungicides
chlozolinate
dichlozoline
drazoxolon
famoxadone
hymexazol
metazoxolon
myclozolin
oxadixyl
vinclozolin
polysulfide fungicides
barium polysulfide
calcium polysulfide
potassium polysulfide
sodium polysulfide
pyrazole fungicides
furametpyr
penthiopyrad
pyridine fungicides
boscalid
buthiobate
dipyrithione
fluazinam
fluopicolide
pyridinitril
pyrifenox
pyroxychlor
pyroxyfur
pyrimidine fungicides
bupirimate
cyprodinil
diflumetorim
dimethirimol
ethirimol
fenarimol
ferimzone
mepanipyrim
nuarimol
pyrimethanil
triarimol
pyrrole fungicides
fenpiclonil
fludioxonil
fluoroimide
quinoline fungicides ethoxyquin
halacrinate
8-hydroxyquinoline sulfate
quinacetol
quinoxyfen
quinone fungicides
benquinox
chloranil
dichlone
dithianon
quinoxaline fungicides
chinomethionat
chlorquinox
thioquinox
thiazole fungicides
ethaboxam
etridiazole
metsulfovax
octhilinone
thiabendazole
thiadifluor
thifluzamide
thiocarbamate fungicides
methasulfocarb
prothiocarb
thiophene fungicides
ethaboxam
silthiofam
triazine fungicides
anilazine
triazole fungicides
amisulbrom
bitertanol
fluotrimazole
triazbutil
see also conazole fungicides (triazoles)
urea fungicides
bentaluron
pencycuron
quinazamid
unclassified fungicides
acibenzolar
acypetacs
allyl alcohol
benzalkonium chloride
benzamacril
bethoxazin
carvone
chloropicrin
DBCP
dehydroacetic acid
diclomezine
diethyl pyrocarbonate
fenaminosulf
fenitropan
fenpropidin
formaldehyde
furfural
hexachlorobutadiene
iodomethane
isoprothiolane
methyl bromide
methyl isothiocyanate
metrafenone
nitrostyrene
nitrothal-isopropyl
OCH 2-phenylphenol
phthalide
piperalin
probenazole
proquinazid
pyroquilon
sodium orthophenylphenoxide
spiroxamine
sultropen
thicyofen
tricyclazole
zinc naphthenate
Insecticides Include, but are not Limited to:
antibiotic insecticides
allosamidin
thuringiensin
  macrocyclic lactone insecticides
  spinosad
    avermectin insecticides
    abamectin
    doramectin
    emamectin
    eprinomectin
    ivermectin
    selamectin
    milbemycin insecticides
    lepimectin
    milbemectin
    milbemycin oxime
    moxidectin
arsenical insecticides
calcium arsenate
copper acetoarsenite
copper arsenate
lead arsenate
potassium arsenite
sodium arsenite
botanical insecticides
anabasine
azadirachtin
d-limonene
nicotine
pyrethrins
  cinerins
    cinerin I
    cinerin II
  jasmolin I
  jasmolin II
  pyrethrin I
    pyrethrin II
quassia
rotenone
ryania
sabadilla
carbamate insecticides
bendiocarb
carbaryl
  benzofuranyl methylcarbamate insecticides
  benfuracarb
  carbofuran
  carbosulfan
  decarbofuran
  furathiocarb
  dimethylcarbamate insecticides
  dimetan
  dimetilan
  hyquincarb pirimicarb
oxime carbamate insecticides
 alanycarb
 aldicarb
 aldoxycarb
 butocarboxim
 butoxycarboxim
 methomyl
 nitrilacarb
 oxamyl
 tazimcarb
 thiocarboxime
 thiodicarb
 thiofanox
phenyl methylcarbamate insecticides
 allyxycarb
 aminocarb
 bufencarb
 butacarb
 carbanolate
 cloethocarb
 dicresyl
 dioxacarb
 EMPC
 ethiofencarb
 fenethacarb
 fenobucarb
 isoprocarb
 methiocarb
 metolcarb
 mexacarbate
 promacyl
 promecarb
 propoxur
 trimethacarb
 XMC
 xylylcarb
dinitrophenol insecticides
 dinex
 dinoprop
 dinosam
 DNOC
fluorine insecticides
 barium hexafluorosilicate
 cryolite
 sodium fluoride
 sodium hexafluorosilicate
 sulfluramid
formamidine insecticides
 amitraz
 chlordimeform
 formetanate
 formparanate
fumigant insecticides
 acrylonitrile
 carbon disulfide
 carbon tetrachloride
 chloroform
 chloropicrin
 para-dichlorobenzene
 1,2-dichloropropane
 ethyl formate
 ethylene dibromide
 ethylene dichloride
 ethylene oxide
 hydrogen cyanide
 iodomethane
 methyl bromide
 methylchloroform
 methylene chloride
 naphthalene
 phosphine
 sulfuryl fluoride
 tetrachloroethane
inorganic insecticides
 borax
 calcium polysulfide
 copper oleate
 mercurous chloride
 potassium thiocyanate
 sodium thiocyanate
 see also arsenical insecticides
 see also fluorine insecticides
insect growth regulators
 chitin synthesis inhibitors
  bistrifluron
  buprofezin
  chlorfluazuron
  cyromazine
  diflubenzuron
  flucycloxuron
  flufenoxuron
  hexaflumuron
  lufenuron
  novaluron
  noviflumuron
  penfluron
  teflubenzuron
  triflumuron
 juvenile hormone mimics
  epofenonane
  fenoxycarb
  hydroprene
  kinoprene
  methoprene
  pyriproxyfen
  triprene
 juvenile hormones
  juvenile hormone I
  juvenile hormone II
  juvenile hormone III
 moulting hormone agonists
  chromafenozide
  halofenozide
  methoxyfenozide
  tebufenozide
 moulting hormones
  α-ecdysone
  ecdysterone
 moulting inhibitors
  diofenolan
 precocenes
  precocene I
  precocene II
  precocene III
 unclassified insect growth regulators
  dicyclanil
nereistoxin analogue insecticides
 bensultap
 cartap
 thiocyclam
 thiosultap
nicotinoid insecticides
 flonicamid nitroguanidine insecticides
  clothianidin
  dinotefuran
  imidacloprid
  thiamethoxam
nitromethylene insecticides
  nitenpyram
  nithiazine
pyridylmethylamine insecticides
  acetamiprid
  imidacloprid
  nitenpyram
  thiacloprid
organochlorine insecticides
  bromo-DDT
  camphechlor
  DDT
    pp'-DDT
  ethyl-DDD
  HCH
    gamma-HCH
    lindane
  methoxychlor
  pentachlorophenol
  TDE
    cyclodiene insecticides
      aldrin
      bromocyclen
      chlorbicyclen
      chlordane
      chlordecone
      dieldrin
      dilor
      endosulfan
      endrin
      HEOD
      heptachlor
      HHDN
      isobenzan
      isodrin
      kelevan
      mirex
organophosphorus insecticides
  organophosphate insecticides
    bromfenvinfos
    chlorfenvinphos
    crotoxyphos
    dichlorvos
    dicrotophos
    dimethylvinphos
    fospirate
    heptenophos
    methocrotophos
    mevinphos
    monocrotophos
    naled
    naftalofos
    phosphamidon
    propaphos
    TEPP
    tetrachlorvinphos
  organothiophosphate insecticides
    dioxabenzofos
    fosmethilan
    phenthoate
    aliphatic organothiophosphate insecticides
      acethion
      amiton
      cadusafos
      chlorethoxyfos
      chlormephos
      demephion
        demephion-O
        demephion-S
      demeton
        demeton-O
        demeton-S
      demeton-methyl
        demeton-O-methyl
        demeton-S-methyl
      demeton-S-methylsulphon
      disulfoton
      ethion
      ethoprophos
      IPSP
      isothioate
      malathion
      methacrifos
      oxydemeton-methyl
      oxydeprofos
      oxydisulfoton
      phorate
      sulfotep
      terbufos
      thiometon
        aliphatic amide organothiophosphate insecticides
        amidithion
        cyanthoate
        dimethoate
        ethoate-methyl
        formothion
        mecarbam
        omethoate
        prothoate
        sophamide
        vamidothion
      oxime organothiophosphate insecticides
        chlorphoxim
        phoxim
        phoxim-methyl
      heterocyclic organothiophosphate insecticides
        azamethiphos
        coumaphos
        coumithoate
        dioxathion
        endothion
        menazon
        morphothion
        phosalone
        pyraclofos
        pyridaphenthion
        quinothion
        benzothiopyran organothiophosphate insecticides
          dithicrofos
          thicrofos
        benzotriazine organothiophosphate insecticides
          azinphos-ethyl
          azinphos-methyl
        isoindole organothiophosphate insecticides
          dialifos
          phosmet
        isoxazole organothiophosphate insecticides
          isoxathion
          zolaprofos pyrazolopyrimidine organothiophosphate insecticides
    chlorprazophos
    pyrazophos
pyridine organothiophosphate insecticides
    chlorpyrifos
    chlorpyrifos-methyl
pyrimidine organothiophosphate insecticides
    butathiofos
    diazinon
    etrimfos
    lirimfos
    pirimiphos-ethyl
    pirimiphos-methyl
    primidophos
    pyrimitate
    tebupirimfos
quinoxaline organothiophosphate insecticides
    quinalphos
    quinalphos-methyl
thiadiazole organothiophosphate insecticides
    athidathion
    lythidathion
    methidathion
    prothidathion
triazole organothiophosphate insecticides
    isazofos
    triazophos
phenyl organothiophosphate insecticides
    azothoate
    bromophos
    bromophos-ethyl
    carbophenothion
    chlorthiophos
    cyanophos
    cythioate
    dicapthon
    dichlofenthion
    etaphos
    famphur
    fenchlorphos
    fenitrothion
    fensulfothion
    fenthion
    fenthion-ethyl
    heterophos
    jodfenphos
    mesulfenfos
    parathion
    parathion-methyl
    phenkapton
    phosnichlor
    profenofos
    prothiofos
    sulprofos
    temephos
    trichlormetaphos-3
    trifenofos
phosphonate insecticides
    butonate
    trichlorfon
phosphonothioate insecticides
    mecarphon
    phenyl ethylphosphonothioate insecticides
        fonofos
        trichloronat
    phenyl phenylphosphonothioate insecticides
        cyanofenphos
        EPN
        leptophos
phosphoramidate insecticides
    crufomate
    fenamiphos
    fosthietan
    mephosfolan
    phosfolan
    pirimetaphos
phosphoramidothioate insecticides
    acephate
    isocarbophos
    isofenphos
    methamidophos
    propetamphos
phosphorodiamide insecticides
    dimefox
    mazidox
    mipafox
    schradan
oxadiazine insecticides
    indoxacarb
phthalimide insecticides
    dialifos
    phosmet
    tetramethrin
pyrazole insecticides
    acetoprole
    ethiprole
    fipronil
    pyrafluprole
    pyriprole
    tebufenpyrad
    tolfenpyrad
    vaniliprole
pyrethroid insecticides
    pyrethroid ester insecticides
        acrinathrin
        allethrin
            bioallethrin
        barthrin
        bifenthrin
        bioethanomethrin
        cyclethrin
        cycloprothrin
        cyfluthrin
            beta-cyfluthrin
        cyhalothrin
            gamma-cyhalothrin
            lambda-cyhalothrin
        cypermethrin
            alpha-cypermethrin
            beta-cypermethrin
            theta-cypermethrin
            zeta-cypermethrin
        cyphenothrin
        deltamethrin
        dimefluthrin
        dimethrin
        empenthrin
        fenfluthrin
        fenpirithrin
        fenpropathrin
        fenvalerate
            esfenvalerate
        flucythrinate fluvalinate
   tau-fluvalinate
furethrin
imiprothrin
metofluthrin
permethrin
   biopermethrin
   transpermethrin
phenothrin
prallethrin
profluthrin
pyresmethrin
resmethrin
   bioresmethrin
   cismethrin
tefluthrin
terallethrin
tetramethrin
tralomethrin
transfluthrin
pyrethroid ether insecticides
   etofenprox
   flufenprox
   halfenprox
   protrifenbute
   silafluofen
pyrimidinamine insecticides
flufenerim
pyrimidifen
pyrrole insecticides
chlorfenapyr
tetronic acid insecticides
spiromesifen
spirotetramat
thiourea insecticides
diafenthiuron
urea insecticides
flucofuron
sulcofuron
see also chitin synthesis inhibitors
unclassified insecticides
closantel
crotamiton
EXD
fenazaflor
fenoxacrim
flubendiamide
hydramethylnon
isoprothiolane
malonoben
metaflumizone
metoxadiazone
nifluridide
pyridaben
pyridalyl
rafoxanide
triarathene
triazamate
Plant Growth Regulators Include, but are not Limited to:
  antiauxins
    clofibric acid
    2,3,5-tri-iodobenzoic acid
  auxins
    4-CPA
    2,4-D
    2,4-DB
    2,4-DEP
    dichlorprop
    fenoprop
    IAA
    IBA
    naphthaleneacetamide
    α-naphthaleneacetic acid
    1-naphthol
    naphthoxyacetic acid
    potassium naphthenate
    sodium naphthenate
    2,4,5-T
  cytokinins
    2iP
    benzyladenine
    kinetin
    zeatin
  defoliants
    calcium cyanamide
    dimethipin
    endothal
    ethephon
    merphos
    metoxuron
    pentachlorophenol
    thidiazuron
    tribufos
  ethylene inhibitors
    aviglycine
    1-methylcyclopropene
  ethylene releasers
    ACC
    etacelasil
    ethephon
    glyoxime
  gibberellins
    gibberellins
    gibberellic acid
  growth inhibitors
    abscisic acid
    ancymidol
    butralin
    carbaryl
    chlorphonium
    chlorpropham
    dikegulac
    flumetralin
    fluoridamid
    fosamine
    glyphosine
    isopyrimol
    jasmonic acid
    maleic hydrazide
    mepiquat
    piproctanyl
    prohydrojasmon
    propham
    2,3,5-tri-iodobenzoic acid
  morphactins
    chlorfluren
    chlorflurenol
    dichlorflurenol
    flurenol
  growth retardants
    chlormequat
    daminozide
    flurprimidol
    mefluidide paclobutrazol
tetcyclacis
uniconazole
growth stimulators
brassinolide
forchlorfenuron
hymexazol
unclassified plant growth regulators
benzofluor
buminafos
carvone
ciobutide
clofencet
cloxyfonac
cyclanilide
cycloheximide
epocholeone
ethychlozate
ethylene
fenridazon
heptopargil
holosulf
inabenfide
karetazan
lead arsenate
methasulfocarb
prohexadione
pydanon
sintofen
triapenthenol
trinexapac The adjuvant of the invention comprises phosphated 2-propylheptanol and/or a phosphated 2-propylheptanol alkoxylate, where the alkoxylate on average comprises 1-20, in another embodiment 2-10, in still another embodiment 2-6, and in still another embodiment 2-4, and most preferably 3, ethyleneoxy units and 0-3, preferably 0-2, propyleneoxy units. In one embodiment, the adjuvant of the invention comprises at least one phosphated alkoxylate according to the formula

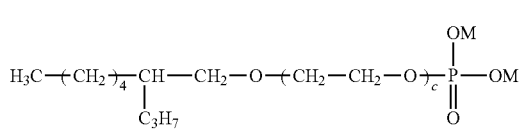

where M is H, a monovalent metal ion or $R_1R_2R_3R_4N^+$, where $R_1$, $R_2$, $R_3$, and $R_4$ are H, an alkyl group with 1-4 carbon atoms or —$CH_2CH_2OH$, and c is a number 1-20, preferably 2-10, more preferably 2-6, even more preferably 2-4, and most preferably 3.

Phosphated 2-propylheptanol or a phosphated 2-propylheptanol alkoxylate may be obtained by different processes, the most common being the reaction of 2-propylheptanol or alkoxylated 2-propylheptanol with polyphosphoric acid or phosphorous pentoxide ($P_2O_5$).

In the process using polyphosphoric acid the resulting product mixture will predominantly contain the monoalkylphosphate ester of 2-propylheptanol or of alkoxylated 2-propylheptanol and only a small amount (<10%) of the dialkylphosphate ester. Always rather large amounts of inorganic phosphate residues from the polyphosphoric acid, such as orthophosphoric acid, will be present.

When $P_2O_5$ is used as the phosphatising reagent and the molar ratio between $P_2O_5$ and alcohol or alkoxylated alcohol is 1:3, the product mixture will contain about equal amounts of monoalkylphosphate ester and dialkylphosphate ester, and only smaller amounts of inorganic phosphate residues. A larger amount of alcohol or alkoxylated alcohol will yield more diester, and a smaller amount will yield more monoester. It will be known to a person skilled in the art how to synthesise phosphate esters with certain amounts of mono- and dialkyl phosphate esters. For a general description of phosphate esters see, e.g., *Anionic Surfactants* Vol. 7, Part II, pages 504-511 in *Surfactant Science Series*, edited by Warner M. Linfield, Marcel Dekker Inc., New York and Basle 1976. The alcohol alkoxylates to be phosphated may be either of the standard type produced by using an alkaline catalyst such as KOH, or of the narrow range type produced by using a narrow range catalyst, such as an acid catalyst, $Ca(OH)_2$ or hydrotalcite.

If necessary, the reaction mixture resulting from either of the procedures can be neutralized by an organic or inorganic base before use. The base may be, e.g., an alkali hydroxide, such as sodium hydroxide or potassium hydroxide; ammonia, an alkanolamine, such as monoethanolamine, triethanolamine or methyldiethanolamine; or an alkylamine such as triethylamine.

The monoalkylphosphate ester of 2-propylheptanol or of ethoxylated 2-propylheptanol has the formula

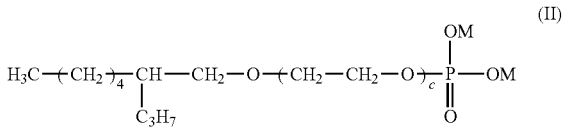

where M is H, a monovalent metal ion or $R_1R_2R_3R_4N^+$, where $R_1$, $R_2$, $R_3$, and $R_4$ are H, an alkyl group with 1-4 carbon atoms or —$CH_2CH_2OH$, and c is a number 0-20, preferably 2-10, more preferably 2-6, even more preferably 2-4, and most preferably 3. The product mixture resulting from the reaction of 2-propylheptanol or of ethoxylated 2-propylheptanol with polyphosphoric acid may also contain smaller amounts of products containing more than one phosphate unit according to the formula

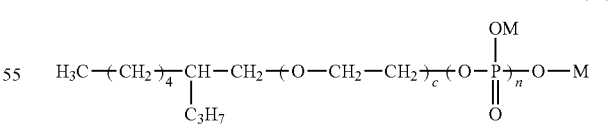

where n is 1-3 and M and c have the same meaning as above.

For ethoxylates containing smaller amounts of ethyleneoxy units, also a certain amount of unethoxylated product will remain due to the distribution of ethyleneoxy units. This unethoxylated product will also be phosphatised during the reaction with the phosphatising agent, and thus the phosphate ester of 2-propylheptanol will also be present in the reaction mixture resulting from these above-mentioned ethoxylates.

The dialkylphosphate ester of 2-propylheptanol has the formula

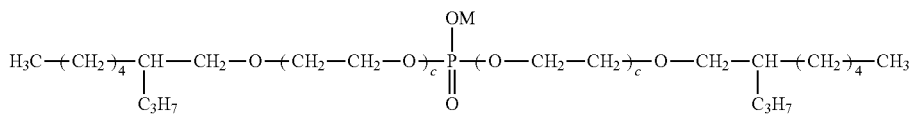

where M and c have the same meaning as above. The product mixture resulting from the reaction of 2-propylheptanol or ethoxylated 2-propylheptanol with $P_2O_5$ may also contain a dialkyl diphosphate ester according to the formula

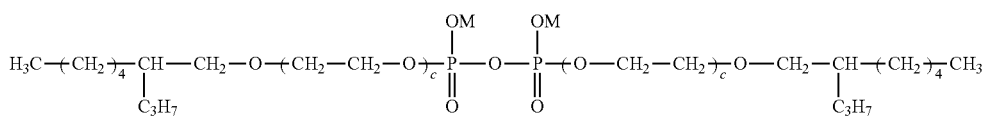

where M and c have the same meaning as above. This type of diester may be hydrolysed to yield 2 moles of monoester.

2-Propylheptanol is normally made by a process resulting in small amounts of by-products such as 4-methyl-2-propylhexanol and 5-methyl-2-propylhexanol. These products or their ethoxylates will also be phosphated during the process, and the phosphated species will be comprised in the resulting product mixture.

The reaction mixtures obtained by the phosphatising procedures are normally used as such without any purification procedure, but both the mixtures and the purified phosphate esters function as hydrotropes. To act as a good hydrotrope, the mixture should predominantly contain the monoalkyl phosphate esters, since these are better hydrotropes than the dialkyl phosphate esters. Preferably more than 60, more preferably more than 70, and most preferably more than 80% by weight of the mixture should be monoalkyl phosphate esters.

The phosphated 2-propylheptanol or phosphated 2-propylheptanol alkoxylates where the alkoxylate on average comprises 1-20, preferably 2-10, more preferably 2-6, even more preferably 2-4, and most preferably 3, ethyleneoxy units and 0-3, preferably 0-2, propyleneoxy and/or butyleneoxy, preferably propyleneoxy, units described above and a process for their production are already partly disclosed in the earlier mentioned publications EP-A-256427 and CH-A-481953 for use as dispersants for pigments and as additives in an emulsion polymerisation process, respectively. However, the phosphated 2-propylheptanol alkoxylate where the alkoxylate comprises 2-4, preferably 3, ethyleneoxy units on average is especially efficient as a hydrotrope compared to the other phosphated alkoxylates of 2-propylheptanol (see Table 1 in the Examples). Therefore, the invention also relates to the phosphated 2-propylheptanol alkoxylate where the alkoxylate on average comprises 2-4, preferably 3, ethyleneoxy units per se and a process for its production.

The agricultural formulations of the invention may contain alkali, preferably sodium or potassium hydroxide, and an alkaline complexing agent that may be inorganic as well as organic. Typical examples of inorganic complexing agents used in the alkaline composition are alkali salts of silicates and phosphates such as sodium silicate, sodium metasilicate, sodium tripolyphosphate, sodium orthophosphate, sodium pyrophosphate, and the corresponding potassium salts. Typical examples of organic complexing agents are alkaline aminopolyphosphonates, organic phosphates, polycarboxylates, such as citrates; aminocarboxylates, such as sodium nitrilotriacetate ($Na_3NTA$), sodium ethylenediaminetetraacetate (EDTA), sodium diethylenetriaminepentaacetate, sodium 1,3-propylenediaminetetraacetate, and sodium hydroxyethylethylenediaminetriacetate. The amount of alkali present in the composition depends on the application and on whether the composition is a concentrate or a ready-to-use solution.

The concentrated compositions of the present invention are stable and in many cases generally clear. The clarity interval is suitably between 0-40° C., preferably between 0-50° C., and most preferably between 0-60° C. This may be adapted by changing the ratio of hydrotrope to nonionic surfactant. The concentrate normally contains 50-95% by weight of water, suitably 70-90% by weight.

To obtain a ready-to-use solution the concentrates are diluted with water and/or fertilizer solutions up to 1:40. The diluted solutions are also clear and stable, but in some cases they may turn a little bit hazy although they are still stable and do not separate. The ready-to-use solutions exhibit good properties. A typical concentrate formulation contains 3-5% by weight of the adjuvant according to the present invention, while a ready-to-use formulation would normally contain 0.2-1% by weight of same.

Tank mixes can include multiple pesticides mixed together, targeting multiple pests, while using water as the delivery medium. In that case the adjuvant would help prevent incompatibilities that could occur when mixing different formulation types together, such as emulsifiable concentrates and suspension concentrates.

Tank mixes can also include pesticide(s) dispersed or emulsified in a fertilizer solution. The adjuvants of the present invention function to facilitate the dispersion or emulsification of the pesticides(s) in the salt solutions by coupling the surfactants into the electrolyte solution.

The present invention is further illustrated by the following Examples.

EXAMPLE 1

This example relates to a comparison between phosphated 2-propylheptanol+5 EO and phosphated hexanol+5 EO as hydrotropes for 2-propylheptanol+5 EO.

TABLE 1

| Compound | Formulation A | Formulation B (Comparison) |
|---|---|---|
| Phosphated 2-PH + 5EO | 3.5% | |
| Phosphated hexanol + 5EO | | 4.9% |
| 2-PH + 5EO | 5.0% | 5.0% |
| Sodium metasilicate | 4.0% | 4.0% |
| Tetrapotassium pyrophosphate | 6.0% | 6.0% |
| Water | 81.5% | 80.1% |

A smaller amount of phosphated 2-propylheptanol+5EO, as compared to phosphated hexanol+5EO, was required to obtain a clarity interval of 0-60° C. The formulations with phosphated 2-propylheptanol+5 EO as a hydrotrope were also much more stable upon dilution.

EXAMPLE 2

This example compares a number of phosphated ethoxylated alcohols with phosphated 2-propylheptanol+5 EO as a hydrotrope for 2-propylheptanol+5 EO.

TABLE 3

| Compound | 1 | 2 (Comparison) | 3 (Comparison) | 4 (Comparison) |
|---|---|---|---|---|
| 2-PH + 5EO | 5.0% | 5.0% | 5.0% | 5.0% |
| Phosphated 2-PH + 5EO | 3.5% | | | |
| Phosphated $C_9$—$C_{11}$-alcohol + 5.5EO | | 3.0% | | |
| Phosphated $C_9$—$C_{11}$-alcohol + 4EO | | | 3.4% | |
| Phosphated 2-ethylhexanol + 4EO | | | | 3.0% |
| Sodium metasilicate | 4.0 | 4.0 | 4.0 | 4.0 |
| Tetra-potassium pyrophosphate | 6.0 | 6.0 | 6.0 | 6.0 |
| Water | 81.5 | 82.0 | 79.0 | 82.0 |

TABLE 4

| Formulation | Clarity interval (° C.) | Appearance after dilution 1:5 after 1 day | Appearance after dilution 1:20 after 1 day | Appearance after dilution 1:5 after 1 week | Appearance after dilution 1:20 after 1 week | Soil removal at 1:20 dilution (%) |
|---|---|---|---|---|---|---|
| 1 | 0-70 | Clear | Clear | Clear | Hazy but stable | 60.0 |
| 2 (Comp.) | 0-53 | Clear | Clear | Clear | Clear | 26.0 |
| 3 (Comp.) | 0-60 | Clear | Clear | Clear | Clear | 44.0 |
| 4 (Comp.) | 0-50 | Hazy | Hazy | Cloudy | Hazy | 54.0 |

The formulation according to the invention exhibited the best cleaning performance of all the investigated formulations, in combination with a good stability upon dilution.

EXAMPLE 3

In this example the wetting ability of a composition according to the invention was measured by the modified Drave's test.

TABLE 5

| Compound | C |
|---|---|
| Phosphated 2-PH + 5EO | 6% |
| $C_9$-$C_{11}$-alcohol + 4EO | 5.0% |
| Sodium nitrilotriacetate | 10.0% |

In the modified Drave's test, the sinking time in s is measured for a specified cotton yarn in approximately 0.1% surfactant solution. The formulation in the Table 5 was diluted with distilled water to 0.1% by weight with respect to the $C_9$-$C_{11}$-alcohol+4 EO, and the modified Drave's test was performed on this solution. The result is displayed in the Table 6, below.

TABLE 6

| Formulation | Clarity interval (° C.) | pH | Sinking time (s) |
|---|---|---|---|
| C | 0-45 | 10.5 | 5 |

The formulation containing the phosphated 2-propylheptanol+5 EO as a hydrotrope for the ethoxylate had a good wetting ability, whereas for the different components alone, the wetting time was >420 s. The $C_9$-$C_{11}$-alcohol is not soluble in this alkaline medium without a hydrotrope, and the phosphated 2-propylheptanol+5 EO has no good wetting ability on its own. When the hydrotrope is added, the nonionic surfactant is solubilised, and it is then able to exert its wetting ability.

EXAMPLE 4

In the syntheses described below a 1,000 cm³ flange flask equipped with an anchor stirrer was used. The reactor was heated by an electrical heater equipped with a thermostat. A slight flow of nitrogen was applied during the reaction. The polyphosphoric acid (PPA) used was Polyphosphoric acid 116, 84% equivalent in $P_2O_5$ (Albright & Wilson).

1) 2-propylheptanol+PPA 2-propylheptanol (222.47 g, 1.41 mole) was charged and heated to 45° C. PPA (254.09 g) was added from a 60 ml syringe and the exothermic reaction was kept at 55-70° C. while stirring at 240 r/min. PPA was added during a period of 1 hour. The reaction was then left for 2 h at 60° C. and with stirring at 300 r/min. After the post-reaction water (5.0 g) was added to hydrolyse the remaining PPA, after which the acid was neutralised with KOH (274.4 g) dissolved in 555.0 g water.

2) 2-propylheptanol+3 EO+PPA 2-propylheptanol+3 EO (295.63 g, 1.02 mole) was charged and heated to 45° C. PPA (184.95 g) was added from a 60 ml syringe and the exothermic reaction was kept at 55-70° C. while stirring at 240 r/min. PPA was added during a period of 1 hour. The reaction was then left for 2 h at 60° C. and with stirring at 300 r/min. After the post-reaction water (5.0 g) was added to hydrolyse the remaining PPA, after which the acid was neutralised with KOH (191 g) dissolved in 454 g water.

3) 2-propylheptanol+5 EO+PPA 2-propylheptanol+5 EO (307.71 g, 0.81 mole) was charged and heated to 45° C. PPA (148 g) was added from a 60 ml syringe and the exothermic reaction was kept at 55-70° C. while stirring at 240 r/min. PPA was added during a period of 1 hour. The reaction was then left for 2 h at 60° C. and with stirring at 300 r/min. After the post reaction water (5.0 g) was added to hydrolyse the remaining PPA, after which 374.02 g acid were neutralised with KOH (132.37 g) dissolved in 517 g water.

EXAMPLE 5

Morwet D-425 is a condensed alkyl naphthalene sulfonate dispersant commercially available from Akzo Nobel Surface Chemistry LLC, Chicago, Ill., that has been used as the main dispersant in various pesticide suspension concentrate, wettable powder and water dispersible granule formulations. Frequently, a nonionic surfactant is used as a cosurfactant to increase the wetting and stability of the formulations. Since the solubility of nonionic surfactants is decreased in the salt solution, flocculation will occur when pesticide formulation is mixed with fertilizer during application. This example is aimed to compare the performance of different cosurfactant in Atrazine SC and to verify if the branched hydrophobe improves the compatibility in ammonium nitrate solution.

Materials

Atrazine Tech.

Morwet D-425 (condensed alkyl naphthalene sulfonate, sodium salt)

Ethylan 1005 phosphate ester (2-propyl heptanol+5EO)

Emphos PS-131 (iso-tridecanol+6EO, phosphate ester, acid form)

Emphos PS-236 (linear C10/12 alcohol+5EO, phosphate ester, acid form)

Witconol SN-70 (linear C10/12 alcohol+5EO)

Witconol TD-60 (iso-tridecanol+6EO)

Ethylan 1005 (2-propyl heptanol+5EO)

Urea-ammonium nitrate

The Atrazine suspensions were made by first dissolving the Morwet D-425 and wetting agent in the appropriate volume of water. Micronized Atrazine technical was then added to the solution and then dispersed using high shear. All of the suspensions tested were made to contain 480 grams per liter of active ingredient.

After preparing the Atrazine suspensions with different surfactant systems, the suspensions were diluted into UAN and evaluated based on the degree of flocculation as a function of time.

Formulations/Results/Observations

TABLE 7

Atrazine formulations with different co surfactants

|  | Atrazine (g) | D-425 (g) | Co surfactant (g) | Water (g) |
|---|---|---|---|---|
| 1996-17-1 | 8.4 | 1.0 | 0.4 (1005 phosphate ester) | 10.2 |
| 1996-17-2 | 8.4 | 1.0 | 0.4 (PS-131) | 10.2 |
| 1996-17-3 | 8.4 | 1.0 | 0.4 (TD-60) | 10.2 |
| 1996-17-4 | 8.4 | 1.0 | 0.4 (Ethylan 1005) | 10.2 |
| 1996-17-5 | 8.4 | 1.0 | 0.4 (PS-236) | 10.2 |
| 1996-17-6 | 8.4 | 1.0 | 0.4 (SN-70) | 10.2 |
| 1996-18-1 | 8.4 | 1.4 | 0.0 | 10.2 |
| 1996-18-2 | 8.4 | 1.0 | 0.0 | 10.6 |
| 1996-18-3 | 8.4 | 0.6 | 0.0 | 11.0 |

Next, 5 mL of each sample were poured in 95 mL of UAN solutions in 100 mL tubes. The tubes were inverted 10 times and observed for flocculation. After sitting for 1, 2, 4, and 24 hours, the height of clear UAN solution from the bottom of tube was measured. The following results were found:

TABLE 8

Atrazine formulation performance in UAN solution

|  | 1 hr (cm) | 2 hr (cm) | 4 hr (cm) | 24 hr (cm) |
|---|---|---|---|---|
| 1996-17-1 | 14.0 | 17. | 20.3 | 24.2 |
| 1996-17-2 | 22.5 | 23.3 | 24.4 | 25.7 |
| 1996-17-3 | 20.5 | 22.0 | 23.1 | 24.9 |
| 1996-17-4 | 19.0 | 20.0 | 21.1 | 22.7 |
| 1996-17-5 | 22.5 | 23.7 | 24.6 | 26.1 |
| 1996-17-6 | 20.0 | 21.0 | 22.1 | 24.4 |
| 1996-18-1 | 0.0 | 0.0 | 0.0 | 3.5 |
| 1996-18-2 | 0.0 | 0.0 | 0.4 | 3.2 |
| 1996-18-3 | 0.0 | 0.0 | 0.2 | 13.4 |

As seen above, all the cosurfactants decreased the SC compatibility in UAN solution because the salt precipitated the cosurfactant from the system. However, Ethylan 1005 phosphate ester (contained in sample 1996-17-1) did perform much better compared to other cosurfactants in the relatively short time period (up to 4 hr).

The difference in the results among formulations was significant enough to indicate that different hydrophobe lengths and branches can play an important role for compatibility issue.

Based on the data generated in this study, Ethylan 1005 phosphate ester showed the potential to improve the SC compatibility with UAN solution.

I claim:

1. An agricultural formulation comprising at least one agricultural active, and at least one agricultural adjuvant, wherein the adjuvant comprises at least one phosphated 2-propylheptanol alkoxylate.

2. The formulation of claim 1 wherein the phosphated 2-propylheptanol alkoxylate on average comprises 1 to 20 ethyleneoxy units and 0-3 propyleneoxy and/or butyleneoxy units.

3. The formulation of claim 1 wherein the phosphated 2-propylheptanol alkoxylate is selected from the group consisting of:

(i) compounds of formula

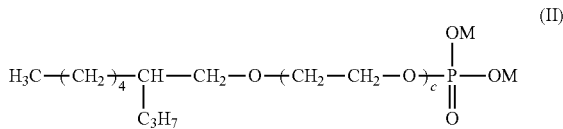

wherein M is H, a monovalent metal ion or $R_1R_2R_3R_4N^+$, where $R_1$, $R_2$, $R_3$, and $R_4$ are H, an alkyl group with 1-4 carbon atoms or —$CH_2CH_2OH$, and c is a number 1-20;

(ii) compounds of formula

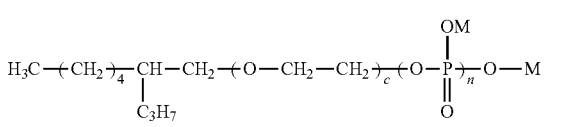

wherein n is 1-3 and M and c are as defined above;

(iii) compounds of formula

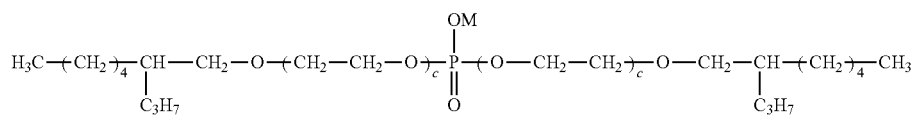

wherein M and c are as defined above;

(iv) compounds of formula

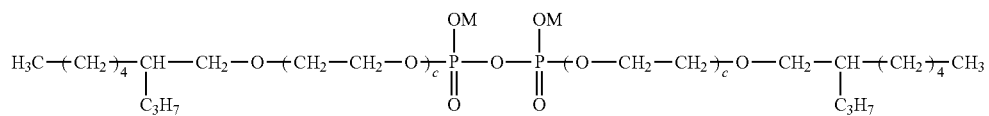

wherein M and c are as defined above; and (v) mixtures thereof.

4. The formulation of claim 1 wherein the phosphated 2-propylheptanol alkoxylate comprises 2 to 4 ethyleneoxy units.

5. The formulation of claim 4 wherein the phosphated alkoxylate is a compound of formula

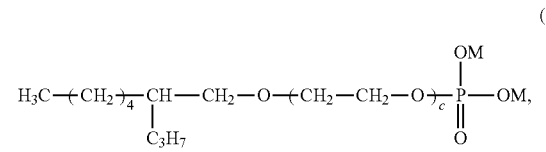

wherein M is H, a monovalent metal ion or $R_1R_2R_3R_4N^+$, where $R_1$, $R_2$, $R_3$, and $R_4$ are H, an alkyl group with 1-4 carbon atoms or —$CH_2CH_2OH$, and c is a number 2-4.

6. The formulation of claim 1 comprising 0.1-30% by weight of the adjuvant, wherein the phosphated 2-propylheptanol alkoxylate on average comprises 1 to 20 ethyleneoxy units and 0-3 propyleneoxy units.

7. The formulation of claim 6, wherein the adjuvant is a phosphated 2-propylheptanol alkoxylate comprising 2-4 ethyleneoxy units.

8. The formulation of claim 1 wherein the adjuvant comprises a mixture of at least one phosphated 2-propylheptanol alkoxylate with at least one phosphated 2-propylheptanol, wherein the phosphated 2-propylheptanol alkoxylate is present in an amount of at least 60% by weight of the adjuvant mixture.

9. The formulation of claim 1 wherein the adjuvant is a dispersant, emulsifier, hydrotrope, wetting agent, and/or compatibility agent.

10. The formulation of claim 1 wherein the agricultural active is a herbicide, fungicide, insecticide, plant growth regulator, or mixtures thereof.

11. An adjuvant for agricultural formulations, wherein the adjuvant comprises at least one phosphated 2-propylheptanol alkoxylate.

12. The adjuvant of claim 11 wherein the phosphated 2-propylheptanol alkoxylate on average comprises 1 to 20 ethyleneoxy units and 0-3 propyleneoxy and/or butyleneoxy units.

13. The adjuvant of claim 11 wherein the phosphated 2-propylheptanol alkoxylate is selected from the group consisting of:

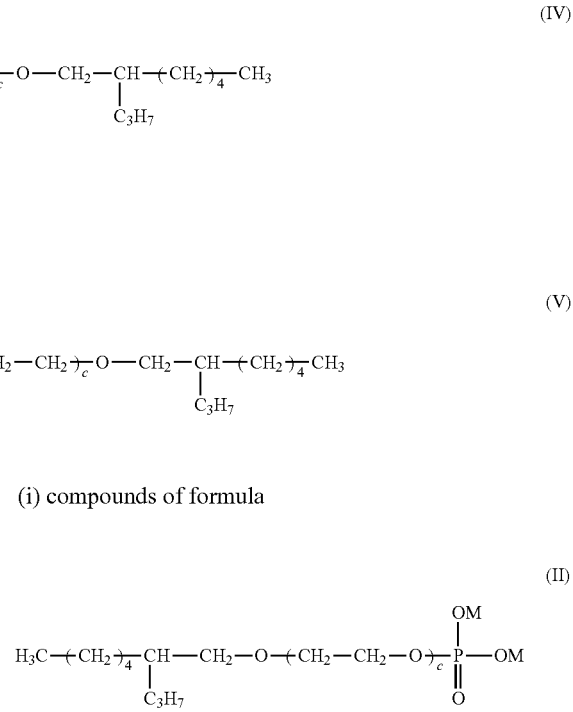

(i) compounds of formula

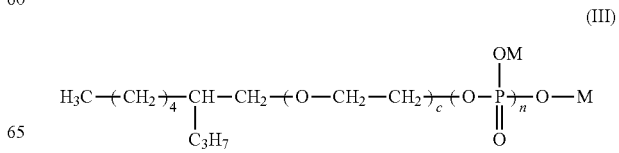

wherein M is H, a monovalent metal ion or $R_1R_2R_3R_4N^+$, where $R_1$, $R_2$, $R_3$, and $R_4$ are H, an alkyl group with 1-4 carbon atoms or —$CH_2CH_2OH$, and c is a number 1-20;

(ii) compounds of formula wherein n is 1-3 and M and c are as defined above;

(iii) compounds of formula

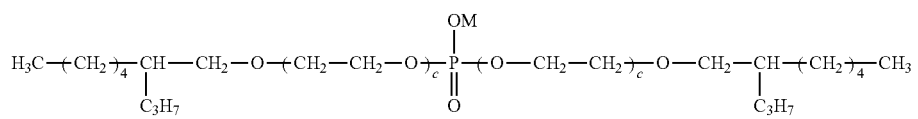
(IV)

wherein M and c are as defined above;

(iv) compounds of formula

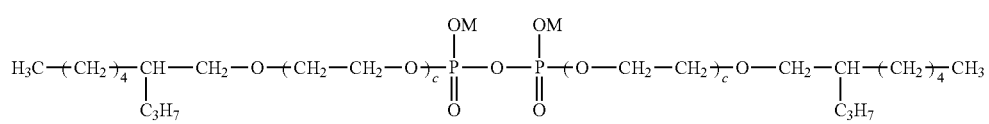
(V)

wherein M and c are as defined above; and (v) mixtures thereof.

14. The adjuvant of claim 11 wherein the phosphated 2-propylheptanol alkoxylate comprises 2 to 4 ethyleneoxy units.

15. The adjuvant of claim 14 wherein the phosphated 2-propylheptanol alkoxylate is a compound of formula

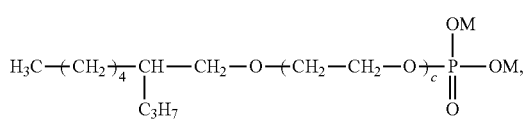
(II)

wherein M is H, a monovalent metal ion or $R_1R_2R_3R_4N^+$, where $R_1$, $R_2$, $R_3$, and $R_4$ are H, an alkyl group with 1-4 carbon atoms or —$CH_2CH_2OH$, and c is a number 2-4.

16. A method of treating plants which comprises contacting the plants with an agriculturally effective amount of the agricultural formulation of claim 1.

* * * * *